(12) United States Patent
Xu et al.

(10) Patent No.: US 12,336,996 B2
(45) Date of Patent: Jun. 24, 2025

(54) DRUG COMBINATION CONTAINING TLR7 AGONIST

(71) Applicant: Chia Tai Tianqing Pharmaceutical Group Co., Ltd., Lianyungang (CN)

(72) Inventors: Hongjiang Xu, Nanjing (CN); Dandan Lu, Nanjing (CN); Xingfeng Ge, Nanjing (CN); Wei Song, Nanjing (CN); Wei Shi, Nanjing (CN); Ling Yang, Nanjing (CN); Xiquan Zhang, Nanjing (CN); Hao Yu, Nanjing (CN); Zhongnan Xu, Nanjing (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 746 days.

(21) Appl. No.: 17/754,099

(22) PCT Filed: Sep. 29, 2020

(86) PCT No.: PCT/CN2020/118693
§ 371 (c)(1),
(2) Date: Mar. 23, 2022

(87) PCT Pub. No.: WO2021/058021
PCT Pub. Date: Apr. 1, 2021

(65) Prior Publication Data
US 2023/0015906 A1    Jan. 19, 2023

(30) Foreign Application Priority Data
Sep. 29, 2019   (CN) .......................... 201910933558.8

(51) Int. Cl.
*A61K 31/519*   (2006.01)
*A61K 9/28*     (2006.01)
*A61K 31/52*    (2006.01)
*A61P 31/12*    (2006.01)

(52) U.S. Cl.
CPC .......... *A61K 31/519* (2013.01); *A61K 9/2893* (2013.01); *A61K 31/52* (2013.01); *A61P 31/12* (2018.01)

(58) Field of Classification Search
CPC ........ A61K 31/519; A61K 31/52; A61P 31/12
USPC .................................................... 514/258.1
See application file for complete search history.

(56) References Cited

FOREIGN PATENT DOCUMENTS

| CN | 102272134 A | 12/2011 |
|---|---|---|
| CN | 105367576 A | 3/2016 |
| EP | 3190113 A1 | 7/2017 |
| EP | 3381918 A1 | 10/2018 |
| JP | 2004-503467 A | 2/2004 |
| JP | 2018-512428 A | 5/2018 |
| WO | WO 2010/150836 A1 | 12/2010 |
| WO | WO 2020/188448 A1 | 9/2020 |

OTHER PUBLICATIONS

Goncalves, Antonio "Modeling HBV kinetics in mice treated by a novel TLR7 agonist, alone or in combination with entecavir" May 2018—https://www.page-meeting.org/default.asp?id=42&keuze=program.
Office Action issued for CN 202080066482.4 issued on Nov. 15, 2024.
Office Action issued for JP 2022-519609 issued on Aug. 18, 2024.
Antonio, Goncalves et al., "Modeling HBV kinetics in mice treated by a novel TLR7 agonist, alone or in a combination with entecavir" Journal of Hepatology, 2019, p. e465, vol. 70, e383-e624.
Chia Tai Tianqing Pharmaceutical Group Co. Ltd., "A Study of TQ-A3334 Combined with Entecavir in the Treatment of Chronic Hepatitis B" Dec. 2019, https://clinicaltrials.gov/ct2/show/NCT04180150.
Korolowizc, Kyle E. et al., "Liver-Targeted Toll-Like Receptor 7 Agonist Combined With Entecavir Promotes a Functional Cure in the Woodchuck Model of Hepatitis B Virus" Hepatology Communications, 2019, pp. 1296-1310, vol. 3, No. 10.
International Search Report for PCT/CN2020/118693 dated Jan. 4, 2021.
Supplementary European Search Report for EP 20870109 issued Sep. 13, 2023.

*Primary Examiner* — Raymond J Henley, III
(74) *Attorney, Agent, or Firm* — Knobbe, Martens, Olson & Bear, LLP

(57) ABSTRACT

A drug combination containing a TLR7 agonist. Specifically, a drug combination jointly using the compound of formula I acting as a TLR7 agonist and entecavir for the treatment of hepatitis B virus infection and a use thereof, the drug combination having a good anti-hepatitis B virus infection effect.

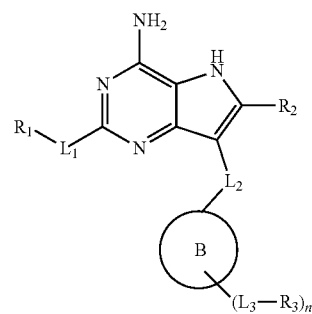

19 Claims, 1 Drawing Sheet

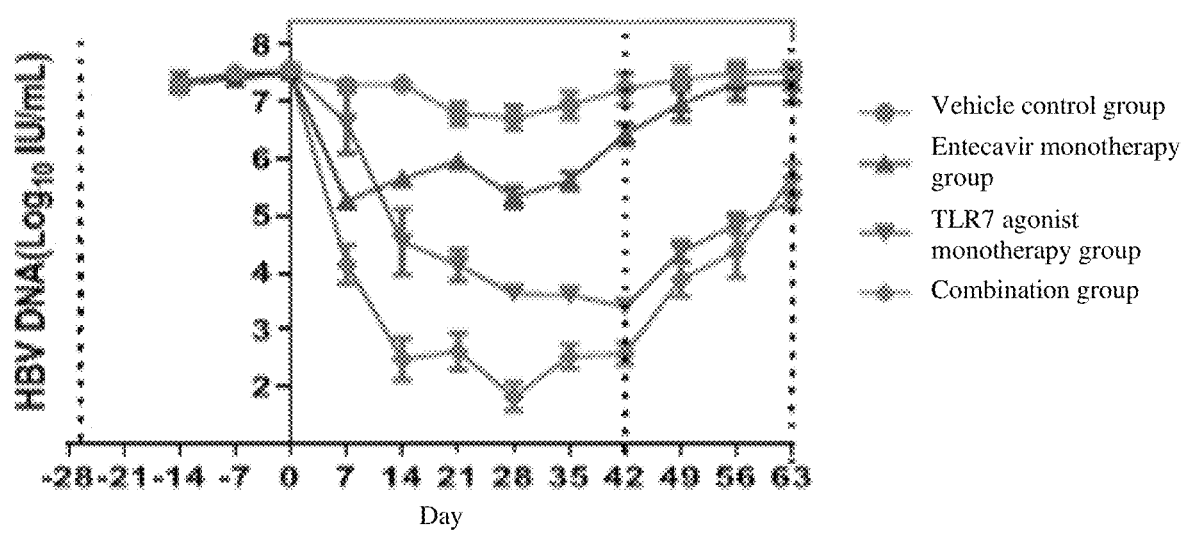

DRUG COMBINATION CONTAINING TLR7 AGONIST

CROSS-REFERENCE TO RELATED APPLICATIONS

This application is a U.S. National Phase Application of PCT International Application Number PCT/CN2020/118693, filed on Sep. 29, 2020, designating the United States of America and published in the Chinese language, which is an International Application of and claims the benefit of priority to Chinese Patent Application No. 201910933558.8, filed on Sep. 29, 2019. The disclosures of the above-referenced applications are hereby expressly incorporated by reference in their entireties.

TECHNICAL FIELD

The present application relates to the field of medicinal chemistry, particularly, to a pharmaceutical combination comprising a TLR7 agonist, and more particularly, to a pharmaceutical combination of a compound of formula I as a TLR7 agonist and entecavir for combined use in treating hepatitis B virus infection and use thereof.

BACKGROUND

As summarized by the World Health Organization, about 257 million people worldwide are infected with hepatitis B virus (HBV). If not well treated, patients with hepatitis will be confronted with long-term fatal diseases such as liver failure, cirrhosis and liver cancer.

Conventional drugs currently approved for the treatment of chronic hepatitis B include nucleosides (nucleotides) and interferons. Nucleosides (nucleotides), such as entecavir, can inhibit HBV DNA replication.

Toll-like receptors are expressed in a variety of immune cells. Toll-like receptors recognize highly conserved structural motifs: pathogen-associated molecular patterns (PAMPs) expressed by microbial pathogens or damage-associated molecular patterns (DAMPs) released by necrotic cells. Toll-like receptors are stimulated by corresponding PAMPs or DAMPs to induce signaling cascade, leading to activation of transcription factors such as AP-1, NF-κB and interferon regulatory factors (impulse response function). As such, a variety of cellular reactions are induced, including production of interferons, proinflammatory cytokines and effector cytokines, thus promoting immune response. 13 toll-like receptors have been found in mammals so far. Toll-like receptors 1, 2, 4, 5 and 6 are mainly expressed on the cell surface while toll-like receptors 3, 7, 8 and 9 are expressed in endosomes. Different toll-like receptors recognize ligands derived from different pathogens. Toll-like receptor 7 (TLR7) is mainly expressed by plasmacytoid dendritic cells (pDCs) and induces secretion of the interferon alpha (IFN-α) by ligand recognition. Some TLR7 agonists have been reported, for example, imiquimod, resiquimod and GS-9620. WO2016023511 and WO2017076346, which are incorporated herein by reference in their entireties, disclose a class of novel TLR7 agonists demonstrating good bioactivity and selectivity.

Although patients with hepatitis B virus infection have many treatment options, there is still a need for more potent therapeutic agents for clinical use.

SUMMARY OF THE INVENTION

In one aspect, the present application provides a pharmaceutical combination, comprising a compound of formula I or a pharmaceutically acceptable salt thereof and entecavir or a pharmaceutically acceptable salt or solvate thereof.

In another aspect, the present application further provides use of the pharmaceutical combination disclosed herein for the manufacture of a medicament for treating hepatitis B virus infection. The present application further provides a method for treating hepatitis B virus infection, comprising administering to a subject in need thereof an effective amount of the pharmaceutical combination disclosed herein. The present application further provides the pharmaceutical combination for use in the treatment of hepatitis B virus infection. The present application further provides use of the pharmaceutical combination disclosed herein for treating hepatitis B virus infection.

In one aspect, the present application provides a pharmaceutical combination, comprising a compound of formula I or a pharmaceutically acceptable salt thereof and entecavir or a pharmaceutically acceptable salt or solvate thereof, the compound of formula I is shown as follows:

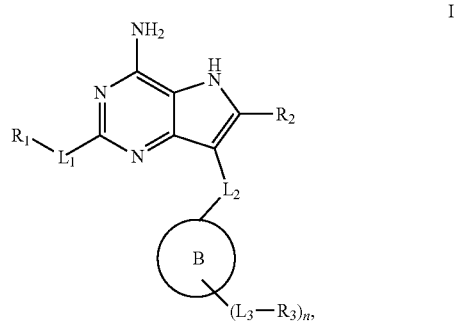

wherein, $L_1$ is selected from —O—;

$L_2$ is selected from —CH$_2$—, wherein the —CH$_2$— is optionally substituted with $R_4$;

$R_1$ is selected from the group consisting of hydrogen and $C_{1-10}$ alkyl, wherein the $C_{1-10}$ alkyl is optionally substituted with $R_5$;

$R_2$ is selected from the group consisting of hydrogen, cyano, —COOH and —CONH$_2$, wherein the —COOH and —CONH$_2$ are optionally substituted with $R_6$;

B is selected from the group consisting of 6-10 membered aryl and 5-10 membered heteroaryl;

$L_3$ is selected from the group consisting of $C_{0-6}$ alkylene and imino, wherein the $C_{0-6}$ alkylene and imino are optionally substituted with $R_7$;

$R_3$ is selected from the group consisting of hydrogen, amino, $C_{1-10}$ alkyl, $C_{3-10}$ cyclohydrocarbyl, 3-10 membered heterocyclohydrocarbyl, 6-10 membered aryl and 5-10 membered heteroaryl, wherein the amino, $C_{1-10}$ alkyl, $C_{3-10}$ cyclohydrocarbyl, 3-10 membered heterocyclohydrocarbyl, 6-10 membered aryl and 5-10 membered heteroaryl are optionally substituted with $R_8$, or $R_3$ and $L_3$, together with an ortho atom on ring B, form a saturated or unsaturated 5-8 membered ring, wherein the 5-8 membered ring is optionally substituted with $R_9$;

n is 0, 1, 2, 3, 4 or 5;

$R_4$, $R_5$, $R_6$, $R_7$, $R_8$ and $R_9$ are each independently selected from halogen, cyano, hydroxy, sulfydryl, amino, —R, —OR, =O, —SR, —NHR and —NR$_2$; R is independently selected from $C_{1-8}$ alkyl, $C_{3-8}$ cyclohydrocarbyl, 3-8 membered heterocyclohydrocarbyl, 6-8 membered aryl and 5-8 membered heteroaryl.

In some embodiments of the compound of formula I, $L_2$ is selected from —$CH_2$—.

In some embodiments of the compound of formula I, $R_1$ is selected from $C_{1-6}$ alkyl, wherein the $C_{1-6}$ alkyl is optionally substituted with one or more $R_5$.

In some embodiments of the compound of formula I, $R_2$ is selected from the group consisting of hydrogen, cyano and —$CONH_2$, wherein the —$CONH_2$ is optionally substituted with one or more $R_6$.

In some embodiments of the compound of formula I, B is selected from the group consisting of 6-7 membered aryl and 5-7 membered heteroaryl. In some embodiments of the compound of formula I, B is selected from the group consisting of phenyl, pyridinyl, pyrimidinyl, pyridazinyl, pyrazinyl, thienyl, thiazolyl, furanyl, oxazolyl, thiadiazolyl, isoxazolyl, oxadiazolyl, pyrrolyl, imidazolyl, pyrazolyl, isothiazolyl and triazolyl. In some embodiments of the compound of formula I, B is selected from the group consisting of phenyl, pyridinyl and thiazolyl.

In some embodiments of the compound of formula I, $L_3$ is selected from $C_{0-6}$ alkylene, wherein the $C_{0-6}$ alkylene is optionally substituted with one or more $R_7$.

In some embodiments of the compound of formula I, $R_3$ is selected from the group consisting of hydrogen, amino, $C_{1-6}$ alkyl, $C_{3-8}$ cyclohydrocarbyl, 3-8 membered heterocyclohydrocarbyl, 6-8 membered aryl and 5-8 membered heteroaryl, wherein the amino, $C_{1-6}$ alkyl, $C_{3-8}$ cyclohydrocarbyl, 3-8 membered heterocyclohydrocarbyl, 6-8 membered aryl and 5-8 membered heteroaryl are optionally substituted with one or more $R_8$; or $R_3$ and $L_3$, together with an ortho atom on ring B, form a saturated or unsaturated 5-8 membered ring, wherein the 5-8 membered ring is optionally substituted with one or more $R_9$. In some embodiments of the compound of formula I, $R_3$ is selected from the group consisting of hydrogen, amino, $C_{1-6}$ alkyl, piperazinyl, morpholinyl, tetrahydropyrrolyl, piperidinyl, azetidinyl, diazepanyl and 2-oxa-5-azabicyclo[2.2.1]heptyl, wherein the amino, $C_{1-6}$ alkyl, piperazinyl, morpholinyl, tetrahydropyrrolyl, piperidinyl, azetidinyl, diazepanyl and 2-oxa-5-azabicyclo[2.2.1]heptyl are optionally substituted with one or more $R_8$; or $R_3$ and $L_3$, together with an ortho atom on ring B, form a saturated or unsaturated 6 membered ring, wherein the 6 membered ring is optionally substituted with one or more $R_9$.

In some embodiments of the compound of formula I, $R_4$, $R_5$, $R_6$, $R_7$, $R_8$ and $R_9$ are each independently selected from the group consisting of halogen, —R, —OR and =O.

In some embodiments of the present application, the compound of formula I or the pharmaceutically acceptable salt thereof is selected from the group consisting of:

2-butoxy-7-(3-((4-methylpiperazin-1-yl)methyl)benzyl)-5H-pyrrolo[3,2-d]pyrimidin-4-amine;
2-butoxy-7-(3-(morpholinomethyl)benzyl)-5H-pyrrolo[3,2-d]pyrimidin-4-amine;
7-(3-(aminomethyl)benzyl)-2-butoxy-5H-pyrrolo[3,2-d]pyrimidin-4-amine;
2-butoxy-7-(3-(pyrrolidin-1-ylmethyl)benzyl)-5H-pyrrolo[3,2-d]pyrimidin-4-amine;
2-butoxy-7-(4-((3,3-difluoropyrrolidin-1-yl)methyl)benzyl)-5H-pyrrolo[3,2-d]pyrimidin-4-amine;
2-butoxy-7-(4-((3-fluoropyrrolidin-1-yl)methyl)benzyl)-5H-pyrrolo[3,2-d]pyrimidin-4-amine;
1-(4-((4-amino-2-butoxy-5H-pyrrolo[3,2-d]pyrimidin-7-yl)methyl)benzyl)pyrrolidin-3-ol;
2-butoxy-7-(4-(piperidin-1-ylmethyl)benzyl)-5H-pyrrolo[3,2-d]pyrimidin-4-amine;
2-butoxy-7-(4-(morpholinomethyl)benzyl)-5H-pyrrolo[3,2-d]pyrimidin-4-amine;
2-butoxy-7-(4-((4-methylpiperazin-1-yl)methyl)benzyl)-5H-pyrrolo[3,2-d]pyrimidin-4-amine;
2-butoxy-7-(4-((dimethylamino)methyl)benzyl)-5H-pyrrolo[3,2-d]pyrimidin-4-amine;
2-butoxy-7-(4-((diethylamino)methyl)benzyl)-5H-pyrrolo[3,2-d]pyrimidin-4-amine;
2-butoxy-7-(4-((dipropylamino)methyl)benzyl)-5H-pyrrolo[3,2-d]pyrimidin-4-amine;
7-(4-(azetidin-1-ylmethyl)benzyl)-2-butoxy-5H-pyrrolo[3,2-d]pyrimidin-4-amine;
2-butoxy-7-(4-((3-methoxyazetidin-1-yl)methyl)benzyl)-5H-pyrrolo[3,2-d]pyrimidin-4-amine;
2-butoxy-7-(4-(4-methyl-1,4-diazepan-1-yl)methyl)benzyl)-5H-pyrrolo[3,2-d]pyrimidin-4-amine;
2-butoxy-7-(4-((2,6-dimethylmorpholino)methyl)benzyl)-5H-pyrrolo[3,2-d]pyrimidin-4-amine;
7-(44(1S,4S)-2-oxa-5-azabicyclo[2.2.1]heptan-5-ylmethyl)benzyl)-2-butoxy-5H-pyrrolo[3,2-d]pyrimidin-4-amine;
2-butoxy-7-(4-((4-methoxypiperidin-1-yl)methyl)benzyl)-5H-pyrrolo[3,2-d]pyrimidin-4-amine;
2-butoxy-7-(4-((4-isopropylpiperazin-1-yl)methyl)benzyl)-5H-pyrrolo[3,2-d]pyrimidin-4-amine;
2-butoxy-7-(4-(pyrrolidin-1-ylmethyl)benzyl)-5H-pyrrolo[3,2-d]pyrimidin-4-amine;
2-butoxy-7-((6-(pyrrolidin-1-ylmethyl)pyridin-3-yl)methyl)-5H-pyrrolo[3,2-d]pyrimidin-4-amine;
2-butoxy-7-(3-(2-(pyrrolidin-1-yl)ethyl)benzyl)-5H-pyrrolo[3,2-d]pyrimidin-4-amine;
2-butoxy-7-(4-(1-(pyrrolidin-1-yl)ethyl)benzyl)-5H-pyrrolo[3,2-d]pyrimidin-4-amine;
2-butoxy-7-(4-(1-methylpiperidin-4-yl)benzyl)-5H-pyrrolo[3,2-d]pyrimidin-4-amine;
2-butoxy-7-(4-(1-methylpyrrolidin-2-yl)benzyl)-5H-pyrrolo[3,2-d]pyrimidin-4-amine;
1-(4-((4-amino-2-butoxy-5H-pyrrolo[3,2-d]pyrimidin-7-yl)methyl)phenyl)-4-methylpiperazin-2-one;
7-benzyl-2-(2-methoxyethoxy)-5H-pyrrolo[3,2-d]pyrimidin-4-amine;
2-(2-methoxyethoxy)-7-((6-methylpyridin-3-yl)methyl)-5H-pyrrolo[3,2-d]pyrimidin-4-amine;
7-((5-chloropyridin-2-yl)methyl)-2-(2-methoxyethoxy)-5H-pyrrolo[3,2-d]pyrimidin-4-amine;
2-(2-methoxyethoxy)-7-((6-(pyrrolidin-1-ylmethyl)pyridin-3-yl)methyl)-5H-pyrrolo[3,2-d]pyrimidin-4-amine;
1-(4-((4-amino-2-(2-methoxyethoxy)-5H-pyrrolo[3,2-d]pyrimidin-7-yl)methyl)phenyl)-4-methylpiperazin-2-one;
2-butoxy-7-((5-(pyrrolidin-1-ylmethyl)pyridin-2-yl)methyl)-5H-pyrrolo[3,2-d]pyrimidin-4-amine;
4-amino-2-butoxy-7-((6-(pyrrolidin-1-ylmethyl)pyridin-3-yl)methyl)-5H-pyrrolo[3,2-d]pyrimidin-6-carbonitrile;
4-amino-2-butoxy-7-(4-(pyrrolidin-1-ylmethyl)benzyl)-5H-pyrrolo[3,2-d]pyrimidin-6-carbonitrile;
4-amino-2-butoxy-7-(4-(morpholinomethyl)benzyl)-5H-pyrrolo[3,2-d]pyrimidin-6-carbonitrile;
4-amino-2-butoxy-7-(4-((4-methylpiperazin-1-yl)methyl)benzyl)-5H-pyrrolo[3,2-d]pyrimidin-6-carbonitrile;
4-amino-2-butoxy-7-(4-(pyrrolidin-1-ylmethyl)benzyl)-5H-pyrrolo[3,2-d]pyrimidin-6-carboxamide;
2-butoxy-7-((1,2,3,4-tetrahydroisoquinolin-7-yl)methyl)-5H-pyrrolo[3,2-d]pyrimidin-4-amine;
2-butoxy-7-((2-methyl-1,2,3,4-tetrahydroisoquinolin-7-yl)methyl)-5H-pyrrolo[3,2-d]pyrimidin-4-amine;

2-butoxy-7-((2-ethyl-1,2,3,4-tetrahydroisoquinolin-7-yl)
methyl)-5H-pyrrolo[3,2-d]pyrimidin-4-amine;
2-butoxy-7-((2-isopropyl-1,2,3,4-tetrahydroisoquinolin-7-yl)methyl)-5H-pyrrolo[3,2-d]pyrimidin-4-amine;
2-butoxy-7-((1,2,3,4-tetrahydroisoquinolin-6-yl)methyl)-5H-pyrrolo[3,2-d]pyrimidin-4-amine;
2-butoxy-7-((2-methyl-1,2,3,4-tetrahydroisoquinolin-6-yl)methyl)-5H-pyrrolo[3,2-d]pyrimidin-4-amine;
2-butoxy-7-((2-ethyl-1,2,3,4-tetrahydroisoquinolin-6-yl)methyl)-5H-pyrrolo[3,2-d]pyrimidin-4-amine; and
2-butoxy-7-((2-(pyrrolidin-1-ylmethyl)thiazol-5-yl)methyl)-5H-pyrrolo[3,2-d]pyrimidin-4-amine, or a pharmaceutically acceptable salt thereof.

In some embodiments of the present application, the compound of formula I or the pharmaceutically acceptable salt thereof is selected from the group consisting of 2-butoxy-7-(4-(pyrrolidin-1-ylmethyl)benzyl)-5H-pyrrolo[3,2-d]pyrimidin-4-amine or a pharmaceutically acceptable salt thereof, and 2-butoxy-7-((2-(pyrrolidin-1-ylmethyl) thiazol-5-yl)methyl)-5H-pyrrolo[3,2-d]pyrimidin-4-amine or a pharmaceutically acceptable salt thereof.

In some embodiments of the present application, the entecavir solvate is selected from an entecavir hydrate. In some embodiments, the entecavir hydrate is selected from the group consisting of entecavir 0.5-2 hydrate. The entecavir hydrate is selected from entecavir monohydrate.

In some embodiments of the present application, the pharmaceutically acceptable salt of entecavir is selected from a maleate salt. In some embodiments of the present application, the pharmaceutically acceptable salt of entecavir is selected from a monomaleate salt.

In some embodiments of the present application, entecavir or the pharmaceutically acceptable salt or solvate thereof is selected from the group consisting of entecavir monomaelate, entecavir monohydrate and entecavir monomaelate monohydrate.

In some embodiments of the present application, the pharmaceutical combination comprises 2-butoxy-7-(4-(pyrrolidin-1-ylmethyl)benzyl)-5H-pyrrolo[3,2-d]pyrimidin-4-amine or a pharmaceutically acceptable salt thereof, and entecavir or a pharmaceutically acceptable salt or solvate thereof. In some embodiments, the pharmaceutical combination disclosed herein comprises 2-butoxy-7-(4-(pyrrolidin-1-ylmethyl)benzyl)-5H-pyrrolo[3,2-d]pyrimidin-4-amine or a maleate or trifluoroacetate salt thereof, and entecavir or a pharmaceutically acceptable salt or hydrate thereof. In some embodiments, the pharmaceutical combination disclosed herein comprises 2-butoxy-7-(4-(pyrrolidin-1-ylmethyl)benzyl)-5H-pyrrolo[3,2-d]pyrimidin-4-amine and entecavir or a monohydrate thereof. In some embodiments of the present application, the pharmaceutical combination comprises 2-butoxy-7-((2-(pyrrolidin-1-ylmethyl)thiazol-5-yl)methyl)-5H-pyrrolo[3,2-d]pyrimidin-4-amine or a pharmaceutically acceptable salt thereof, and entecavir or a solvate thereof. In some embodiments, the pharmaceutical combination disclosed herein comprises 2-butoxy-7-((2-(pyrrolidin-1-ylmethyl)thiazol-5-yl)methyl)-5H-pyrrolo[3,2-d]pyrimidin-4-amine and entecavir monomaleate monohydrate.

In some embodiments of the present application, the compound of formula I or the pharmaceutically acceptable salt thereof in the pharmaceutical combination can be administered once every day, twice every day, once every two days, once every three days, once every four days, or once every five days, at a dose of 0.0001 to 20 mg/kg body weight (on the basis of the weight of the compound of formula I).

In some embodiments of the present application, entecavir or the pharmaceutically acceptable salt or solvate thereof in the pharmaceutical combination can be administered once every day, twice every day, or once every two days, at a dose of 0.5 mg or 1.0 mg (on the basis of the weight of entecavir).

In some embodiments of the present application, an average daily dose of entecavir or the pharmaceutically acceptable salt or solvate thereof in the pharmaceutical combination is 0.005 mg to 10.0 mg. In some embodiments of the present application, the average daily dose of entecavir or the pharmaceutically acceptable salt or solvate thereof in the pharmaceutical combination is 0.05 mg to 5.0 mg. In some embodiments of the present application, the average daily dose of entecavir or the pharmaceutically acceptable salt or solvate thereof in the pharmaceutical combination is 0.10 mg to 2.0 mg. In some embodiments of the present application, the average daily dose of entecavir or the pharmaceutically acceptable salt or solvate thereof in the pharmaceutical combination is 0.25 mg to 2.0 mg. In some embodiments of the present application, the average daily dose of entecavir or the pharmaceutically acceptable salt or solvate thereof in the pharmaceutical combination is 0.5 mg to 1.0 mg.

In some embodiments of the present application, an average daily dose ratio (on weight basis) of the compound of formula I or the pharmaceutically acceptable salt thereof to entecavir or the pharmaceutically acceptable salt or solvate thereof in the pharmaceutical combination is selected from 10:1 to 1:10. In some embodiments, the average daily dose ratio (on weight basis) of the compound of formula I or the pharmaceutically acceptable salt thereof to entecavir or the pharmaceutically acceptable salt or solvate thereof is selected from the group consisting of 10:1, 9:1, 8:1, 7:1, 6:1, 5:1, 4:1, 3:1, 2:1, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9, 1:10, and a range formed by any of the ratios. In some embodiments, the average daily dose ratio (on weight basis) of the compound of formula I or the pharmaceutically acceptable salt thereof to entecavir or the pharmaceutically acceptable salt or solvate thereof is preferably selected from the group consisting of 1:1.5 to 1:4, 1:1.6 to 1:3.8, 1:1.8 to 1:3.8, 1:1.8 to 1:3.6 and 1:2 to 1:3.5.

In some embodiments of the present application, the pharmaceutical combination is a fixed combination. In some embodiments, the fixed combination is in the form of a solid pharmaceutical composition. In some embodiments, the compound of formula I or the pharmaceutically acceptable salt thereof and entecavir or the pharmaceutically acceptable salt or solvate thereof in the fixed combination are present in the same solid pharmaceutical composition.

In some embodiments of the present application, the pharmaceutical combination is a non-fixed combination. In some embodiments, the compound of formula I or the pharmaceutically acceptable salt thereof and entecavir or the pharmaceutically acceptable salt or solvate thereof in the non-fixed combination are each in the form of a solid pharmaceutical composition. In some embodiments, the compound of formula I or the pharmaceutically acceptable salt thereof and entecavir or the pharmaceutically acceptable salt or solvate thereof in the non-fixed combination are each in the form of a solid pharmaceutical composition, and the solid pharmaceutical composition of the compound of formula I or the pharmaceutically acceptable salt thereof and the solid pharmaceutical composition of entecavir or the pharmaceutically acceptable salt or solvate thereof are present in the same sachet. In some embodiments, the compound of formula I or the pharmaceutically acceptable salt thereof and entecavir or the pharmaceutically acceptable salt or solvate thereof in the non-fixed combination are each in the form of a solid pharmaceutical composition, and the solid pharmaceutical composition of the compound of formula I or the pharmaceutically acceptable salt thereof and the solid pharmaceutical composition of entecavir or the pharmaceutically acceptable salt or solvate thereof are not present in the same sachet.

In some embodiments of the present application, the solid pharmaceutical composition is selected from the group consisting of a tablet and a capsule.

In another aspect, the present application further provides use of the pharmaceutical combination disclosed herein for the manufacture of a medicament for treating hepatitis B virus infection. The pharmaceutical combination is as described above.

In another aspect, the present application further provides a method for treating hepatitis B virus infection, comprising administering to a subject in need thereof an effective amount of the pharmaceutical combination disclosed herein. The pharmaceutical combination is as described above.

In another aspect, the present application further provides the pharmaceutical combination disclosed herein for use in the treatment of hepatitis B virus infection. The pharmaceutical combination is as described above.

In another aspect, the present application further provides use of the pharmaceutical combination disclosed herein for treating hepatitis B virus infection. The pharmaceutical combination is as described above.

In some embodiments of the present application, the present application provides use of the compound of formula I or the pharmaceutically acceptable salt thereof and entecavir or the pharmaceutically acceptable salt or solvate thereof in preparing a medicament for treating hepatitis B virus infection, wherein the compound of formula I or the pharmaceutically acceptable salt thereof and entecavir or the pharmaceutically acceptable salt or solvate thereof are separately prepared into pharmaceutical compositions.

In some embodiments of the present application, the present application further provides a kit for treating hepatitis B virus infection, comprising: (a) a first pharmaceutical composition comprising the compound of formula I or the pharmaceutically acceptable salt thereof as active ingredient; (b) a second pharmaceutical composition comprising entecavir or the solvate thereof as active ingredient; and optionally, (c) a package insert for combined use of the compound of formula I or the pharmaceutically acceptable salt thereof and entecavir or the pharmaceutically acceptable salt or solvate thereof.

Compound of Formula I or Pharmaceutically Acceptable Salt Thereof, or Pharmaceutical Composition Thereof In some embodiments, the compound of formula I or the pharmaceutically acceptable salt thereof is selected from a compound of formula A or a pharmaceutically acceptable salt thereof:

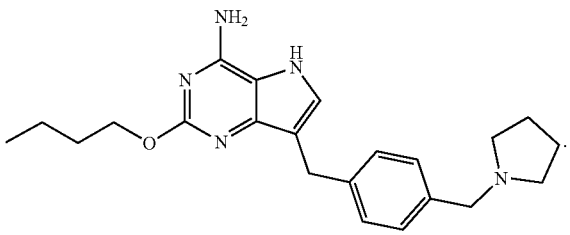

The compound of formula A is known in the prior art and has the chemical name 2-butoxy-7-(4-(pyrrolidin-1-ylmethyl)benzyl)-5H-pyrrolo[3,2-d]pyrimidin-4-amine, of which the preparation and chemical properties are described in WO2016023511.

In some embodiments, the pharmaceutically acceptable salt of the compound of formula A is selected from the group consisting of a maleate salt or a fumarate salt.

In some embodiments, the pharmaceutical composition of the compound of formula A or the pharmaceutically acceptable salt thereof is selected from a solid pharmaceutical composition, preferably selected from the group consisting of a tablet and a capsule.

In some embodiments, the compound of formula A or the pharmaceutically acceptable salt thereof is in the form of a pharmaceutical composition having a unit dose of 0.01 mg to 10 mg, preferably a pharmaceutical composition having a unit dose of 0.01 mg, 0.02 mg, 0.05 mg, 0.08 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, 10.0 mg, or a range formed by any of the values.

Entecavir or Pharmaceutically Acceptable Salt or Solvate Thereof, or Pharmaceutical Composition Thereof As used herein, entecavir has the chemical name 2-amino-9-[(1S,3R,4S)-4-hydroxy-3-hydroxymethyl-2-methylenecyclopentyl]-1,9-dihydro-6H-purin-6-one and the following structural formula:

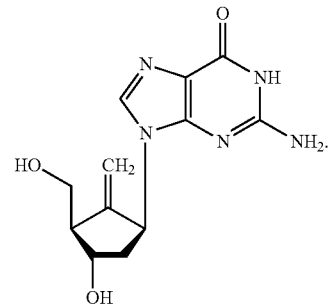 [SMILES: C=C1[C@H](CO)[C@H](O)C[C@@H]1n1cnc2c(=O)[nH]c(N)nc21]

In some embodiments, entecavir comprises a pharmaceutically acceptable salt thereof selected from a maleate salt.

In some embodiments, the pharmaceutically acceptable salt of entecavir is selected from a monomaleate salt.

In some embodiments, entecavir comprises a solvate thereof selected from an entecavir hydrate. In some embodiments, the entecavir hydrate is selected from the group consisting of entecavir 0.5-2 hydrate. In some embodiments, the entecavir hydrate is selected from entecavir monohydrate.

In some embodiments, entecavir is selected from the group consisting of entecavir monomaelate, entecavir monohydrate and entecavir monomaelate monohydrate.

In some embodiments, entecavir or the pharmaceutically acceptable salt or solvate thereof is in the form of a pharmaceutical composition. Preferably, the pharmaceutical composition is selected from a solid pharmaceutical composition. The solid pharmaceutical composition is preferably selected from the group consisting of a tablet and a capsule.

In some embodiments, the pharmaceutical composition of entecavir or the pharmaceutically acceptable salt or solvate thereof is selected from a pharmaceutical composition having a unit dose of 0.01 mg to 5 mg, preferably selected from a pharmaceutical composition having a unit dose of 0.01 mg, 0.02 mg, 0.05 mg, 0.08 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, or a range formed by any of the values.

As used herein, entecavir or the pharmaceutically acceptable salt or solvate thereof, or the pharmaceutical composition thereof may be selected from a commercially available product.

Definitions and Description

Unless otherwise stated, the following terms used herein shall have the following meanings. A certain term, unless otherwise specifically defined, should not be considered uncertain or unclear, but construed according to its common meaning in the field.

As used herein, the compound of formula I or the pharmaceutically acceptable salt thereof is a TLR7 agonist.

As used herein, entecavir has the chemical name 2-amino-9-[(1S,3R,4S)-4-hydroxy-3-hydroxymethyl-2-methylenecyclopentyl]-1,9-dihydro-6H-purin-6-one and the following structural formula:

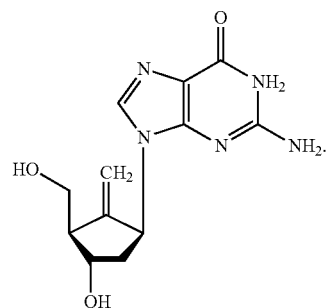 [SMILES: C=C1[C@H](CO)[C@H](O)C[C@@H]1n1cnc2c(=O)[nH]c(N)nc21]

As used herein, structural formulas and chemical names of a portion of the compounds of formula I or the pharmaceutically acceptable salts thereof are as follows:

| Name/Number | Structural formula | Chemical name |
|---|---|---|
| 1 | 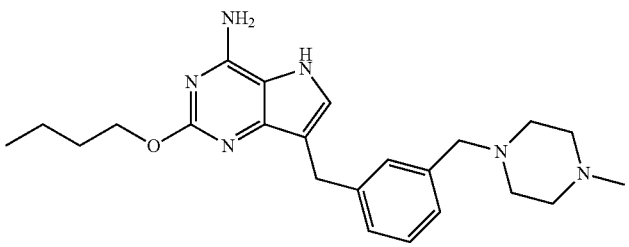 [SMILES: CCCCOc1nc(N)c2[nH]cc(Cc3cccc(CN4CCN(C)CC4)c3)c2n1] | 2-butoxy-7-(3-((4-methylpiperazin-1-yl)methyl)benzyl)-5H-pyrrolo[3,2-d]pyrimidin-4-amine |
| 2 | 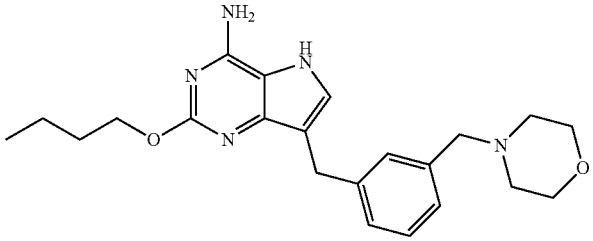 [SMILES: CCCCOc1nc(N)c2[nH]cc(Cc3cccc(CN4CCOCC4)c3)c2n1] | 2-butoxy-7-(3-(morpholinomethyl)benzyl)-5H-pyrrolo[3,2-d]pyrimidin-4-amine |

-continued

| Name/Number | Structural formula | Chemical name |
|---|---|---|
| 3 | | 7-(3-(aminomethyl)benzyl)-2-butoxy-5H-pyrrolo[3,2-d]pyrimidin-4-amine |
| 4 | | 2-butoxy-7-(3-(pyrrolidin-1-ylmethyl)benzyl)-5H-pyrrolo[3,2-d]pyrimidin-4-amine |
| 5 | | 2-butoxy-7-(4-((3,3-difluoropyrrolidin-1-yl)methyl)benzyl)-5H-pyrrolo[3,2-d]pyrimidin-4-amine |
| 6 | | 2-butoxy-7-(4-((3-fluoropyrrolidin-1-yl)methyl)benzyl)-5H-pyrrolo[3,2-d]pyrimidin-4-amine |
| 7 | | 1-(4-((4-amino-2-butoxy-5H-pyrrolo[3,2-d]pyrimidin-7-yl)methyl)benzyl)pyrrolidin-3-ol |
| 8 | | 2-butoxy-7-(4-(piperidin-1-ylmethyl)benzyl)-5H-pyrrolo[3,2-d]pyrimidin-4-amine |

-continued

| Name/Number | Structural formula | Chemical name |
|---|---|---|
| 9 | 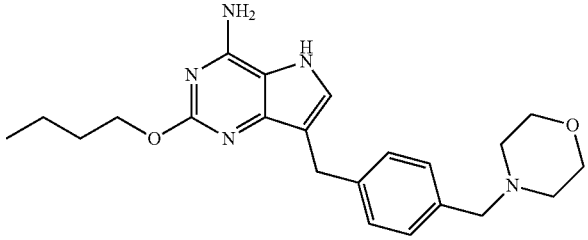 [SMILES: CCCCOc1nc(N)c2[nH]cc(Cc3ccc(CN4CCOCC4)cc3)c2n1] | 2-butoxy-7-(4-(morpholinomethyl)benzyl)-5H-pyrrolo[3,2-d]pyrimidin-4-amine |
| 10 | 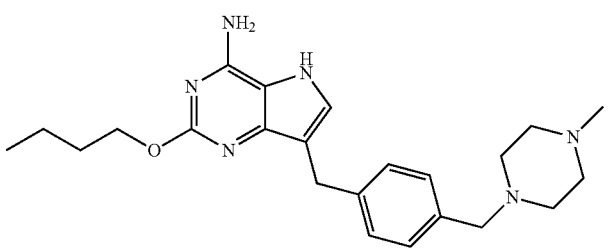 [SMILES: CCCCOc1nc(N)c2[nH]cc(Cc3ccc(CN4CCN(C)CC4)cc3)c2n1] | 2-butoxy-7-(4-((4-methylpiperazin-1-yl)methyl)benzyl)-5H-pyrrolo[3,2-d]pyrimidin-4-amine |
| 11 | 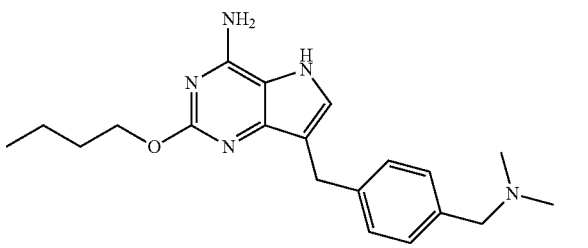 [SMILES: CCCCOc1nc(N)c2[nH]cc(Cc3ccc(CN(C)C)cc3)c2n1] | 2-butoxy-7-(4-((dimethylamino)methyl)benzyl)-5H-pyrrolo[3,2-d]pyrimidin-4-amine |
| 12 | 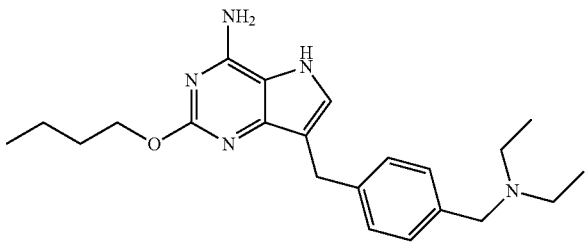 [SMILES: CCCCOc1nc(N)c2[nH]cc(Cc3ccc(CN(CC)CC)cc3)c2n1] | 2-butoxy-7-(4-((diethylamino)methyl)benzyl)-5H-pyrrolo[3,2-d]pyrimidin-4-amine |
| 13 | 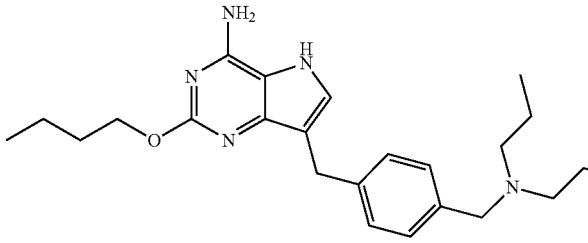 | 2-butoxy-7-(4-((dipropylamino)methyl)benzyl)-5H-pyrrolo[3,2-d]pyrimidin-4-amine |
| 14 | 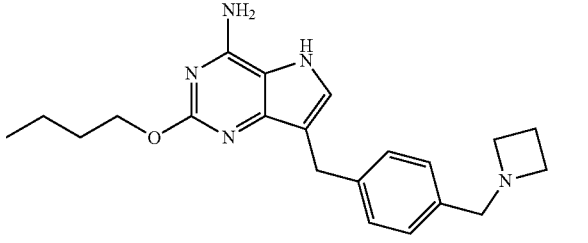 [SMILES: CCCCOc1nc(N)c2[nH]cc(Cc3ccc(CN4CCC4)cc3)c2n1] | 7-(4-(azetidin-1-ylmethyl)benzyl)-2-butoxy-5H-pyrrolo[3,2-d]pyrimidin-4-amine |

-continued

| Name/Number | Structural formula | Chemical name |
|---|---|---|
| 15 | | 2-butoxy-7-(4-((3-methoxyazetidin-1-yl)methyl)benzyl)-5H-pyrrolo[3,2-d]pyrimidin-4-amine |
| 16 | | 2-butoxy-7-(4-((4-methyl-1,4-diazepan-1-yl)methyl)benzyl)-5H-pyrrolo[3,2-d]pyrimidin-4-amine |
| 17 | | 2-butoxy-7-(4-((2,6-dimethylmorpholino)methyl)benzyl)-5H-pyrrolo[3,2-d]pyrimidin-4-amine |
| 18 | | 7-(4-((1S,4S)-2-oxa-5-azabicyclo[2.2.1]heptan-5-ylmethyl)benzyl)-2-butoxy-5H-pyrrolo[3,2-d]pyrimidin-4-amine |
| 19 | | 2-butoxy-7-(4-((4-methoxypiperidin-1-yl)methyl)benzyl)-5H-pyrrolo[3,2-d]pyrimidin-4-amine |
| 20 | | 2-butoxy-7-(4-((4-isopropylpiperazin-1-yl)methyl)benzyl)-5H-pyrrolo[3,2-d]pyrimidin-4-amine |

-continued

| Name/Number | Structural formula | Chemical name |
|---|---|---|
| 21 | | 2-butoxy-7-(4-(pyrrolidin-1-ylmethyl)benzyl)-5H-pyrrolo[3,2-d]pyrimidin-4-amine |
| 22 | | 2-butoxy-7-((6-(pyrrolidin-1-ylmethyl)pyridin-3-yl)methyl)-5H-pyrrolo[3,2-d]pyrimidin-4-amine |
| 23 | | 2-butoxy-7-(3-(2-(pyrrolidin-1-yl)ethyl)benzyl)-5H-pyrrolo[3,2-d]pyrimidin-4-amine |
| 24 | | 2-butoxy-7-(4-(1-(pyrrolidin-1-yl)ethyl)benzyl)-5H-pyrrolo[3,2-d]pyrimidin-4-amine |
| 25 | | 2-butoxy-7-(4-(1-methylpiperidin-4-yl)benzyl)-5H-pyrrolo[3,2-d]pyrimidin-4-amine |
| 26 | | 2-butoxy-7-(4-(1-methylpyrrolidin-2-yl)benzyl)-5H-pyrrolo[3,2-d]pyrimidin-4-amine |

-continued

| Name/Number | Structural formula | Chemical name |
|---|---|---|
| 27 | | 1-(4-((4-amino-2-butoxy-5H-pyrrolo[3,2-d]pyrimidin-7-yl)methyl)phenyl)-4-methylpiperazin-2-one |
| 28 | | 7-benzyl-2-(2-methoxyethoxy)-5H-pyrrolo[3,2-d]pyrimidin-4-amine |
| 29 | | 2-(2-methoxyethoxy)-7-((6-methylpyridin-3-yl)methyl)-5H-pyrrolo[3,2-d]pyrimidin-4-amine |
| 30 | | 7-((5-chloropyridin-2-yl)methyl)-2-(2-methoxyethoxy)-5H-pyrrolo[3,2-d]pyrimidin-4-amine |
| 31 | | 2-(2-methoxyethoxy)-7-((6-(pyrrolidin-1-ylmethyl)pyridin-3-yl)methyl)-5H-pyrrolo[3,2-d]pyrimidin-4-amine |
| 32 | | 1-(4-((4-amino-2-(2-methoxyethoxy)-5H-pyrrolo[3,2-d]pyrimidin-7-yl)methyl)phenyl)-4-methylpiperazin-2-one |

| Name/Number | Structural formula | Chemical name |
|---|---|---|
| 33 | | 2-butoxy-7-((5-(pyrrolidin-1-ylmethyl)pyridin-2-yl)methyl)-5H-pyrrolo[3,2-d]pyrimidin-4-amine |
| 34 | | 4-amino-2-butoxy-7-((6-(pyrrolidin-1-ylmethyl)pyridin-3-yl)methyl)-5H-pyrrolo[3,2-d]pyrimidin-6-carbonitrile |
| 35 | | 4-amino-2-butoxy-7-(4-(pyrrolidin-1-ylmethyl)benzyl)-5H-pyrrolo[3,2-d]pyrimidin-6-carbonitrile |
| 36 | | 4-amino-2-butoxy-7-(4-(morpholinomethyl)benzyl)-5H-pyrrolo[3,2-d]pyrimidin-6-carbonitrile |
| 37 | | 4-amino-2-butoxy-7-(4-((4-methylpiperazin-1-yl)methyl)benzyl)-5H-pyrrolo[3,2-d]pyrimidin-6-carbonitrile |
| 38 | | 4-amino-2-butoxy-7-(4-(pyrrolidin-1-ylmethyl)benzyl)-5H-pyrrolo[3,2-d]pyrimidin-6-carboxamide |

-continued

| Name/Number | Structural formula | Chemical name |
|---|---|---|
| 39 | | 2-butoxy-7-((1,2,3,4-tetrahydroisoquinolin-7-yl)methyl)-5H-pyrrolo[3,2-d]pyrimidin-4-amine |
| 40 | | 2-butoxy-7-((2-methyl-1,2,3,4-tetrahydroisoquinolin-7-yl)methyl)-5H-pyrrolo[3,2-d]pyrimidin-4-amine |
| 41 | | 2-butoxy-7-((2-ethyl-1,2,3,4-tetrahydroisoquinolin-7-yl)methyl)-5H-pyrrolo[3,2-d]pyrimidin-4-amine |
| 42 | | 2-butoxy-7-((2-isopropyl-1,2,3,4-tetrahydroisoquinolin-7-yl)methyl)-5H-pyrrolo[3,2-d]pyrimidin-4-amine |
| 43 | | 2-butoxy-7-((1,2,3,4-tetrahydroisoquinolin-6-yl)methyl)-5H-pyrrolo[3,2-d]pyrimidin-4-amine |
| 44 | | 2-butoxy-7-((2-methyl-1,2,3,4-tetrahydroisoquinolin-6-yl)methyl)-5H-pyrrolo[3,2-d]pyrimidin-4-amine |

| Name/Number | Structural formula | Chemical name |
|---|---|---|
| 45 | | 2-butoxy-7-((2-ethyl-1,2,3,4-tetrahydroisoquinolin-6-yl)methyl)-5H-pyrrolo[3,2-d]pyrimidin-4-amine |
| 46 | | 2-butoxy-7-((2-(pyrrolidin-1-ylmethyl)thiazol-5-yl)methyl)-5H-pyrrolo[3,2-d]pyrimidin-4-amine |

As used herein, the compound of formula I includes non-salt forms thereof (for example, free acids or free bases) and further includes pharmaceutically acceptable salts thereof. The non-salts or salts fall within the scope of protection of the present application. For example, the pharmaceutically acceptable salt of the compound of formula I may be a hydrochloride salt, a maleate salt or a fumarate salt.

As used herein, entecavir includes non-solvate forms thereof and further includes solvate forms thereof. The non-solvates or solvates fall within the scope of protection of the present application. When selected from solvate forms, the molar ratio of the compound to the solvent may be selected from the group consisting of 1:0.5, 1:1, 1:1.5, 1:2, or a range formed by any of the ratios, e.g., 1:0.5 to 1:2, 1:0.5 to 1:1.5, or 1:1 to 1:1.5. For example, entecavir is in the form of a non-solvate. For example, entecavir is in the form of a hydrate. For example, entecavir is in the form of a monohydrate.

As used herein, the dose is based on the weight of the free form of the compound, the free form of the compound referring to the non-salt and non-solvate form of the compound.

The term "substitute" or "substituted" means that any one or more hydrogen atoms on a specific atom are substituted with substituents, as long as the valence of the specific atom is normal and the resulting compound is stable. When the substituent is oxo (namely =O), it means that two hydrogen atoms are substituted, and oxo is not available on an aromatic group.

The term "optional" or "optionally" means that the subsequently described event or circumstance may or may not occur. The description includes instances where the event or circumstance occurs and instances where the event or circumstance does not occur. For example, an ethyl optionally substituted with halogen, means that the ethyl may be unsubstituted ($CH_2CH_3$), monosubstituted (for example, $CH_2CH_2F$), polysubstituted (for example, $CHFCH_2F$, $CH_2CHF_2$ and the like) or fully substituted ($CF_2CF_3$). It will be understood by those skilled in the art that for any groups comprising one or more substituents, any substitutions or substituting patterns which may not exist spatially or cannot be synthesized are not introduced.

$C_{m-n}$ used herein means that the portion has an integer number of carbon atoms in the given range. For example, "$C_{1-6}$" means that the group may have 1 carbon atom, 2 carbon atoms, 3 carbon atoms, 4 carbon atoms, 5 carbon atoms or 6 carbon atoms.

When any variable (e.g., R) occurs more than once in the constitution or structure of a compound, the variable is independently defined in each case. Therefore, for example, if a group is substituted with 2 Rs, the R has independent option at each case.

When the number of a linking group is 0, for example, —$(CH_2)_0$—, it means that the linking group is a covalent bond. When a bond of a substituent is cross-linked to two atoms on a ring, the substituent can be bonded to any atom on the ring. For example, structural unit

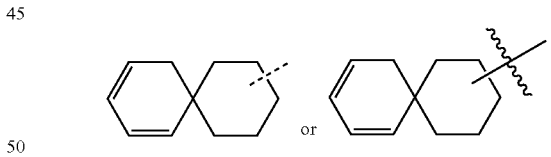

represents that substitution may occur at any one position of cyclohexyl or cyclohexadienyl.

The term "halo-" or "halogen" refers to fluorine, chlorine, bromine and iodine.

The term "hydroxyl" refers to —OH group.
The term "cyano" refers to —CN group.
The term "sulfydryl" refers to —SH group.
The term "amino" refers to —$NH_2$ group.
The term "alkyl" refers to hydrocarbyl with a general formula of $C_nH_{2n+1}$. The alkyl can be linear or branched. For example, the term "$C_{1-6}$ alkyl" refers to alkyl with 1-6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). Similarly, the alkyl portions (namely alkyl) of alkoxyl, monoalkylamine, dialkylamine, alkylsulfonyl and alkylsulfanyl have the same meaning as defined above.

The term "alkoxyl" refers to —O-alkyl.

The term "cycloalkyl" refers to a carbon ring that is fully saturated and may exist as a monocyclic, bridged cyclic or spiro cyclic structure. Unless otherwise specified, the carbon ring is generally a 3-10 membered ring. Non-limiting examples of cycloalkyl include, but are not limited to, cyclopropyl, cyclobutyl, cyclopentyl, cyclohexyl, norbornyl (bicyclo[2.2.1]heptyl), bicyclo[2.2.2]octyl, adamantyl, and the like.

The term "cyclohydrocarbyl" refers to a saturated or unsaturated nonaromatic cyclic hydrocarbyl consisting of carbon atoms and hydrogen atoms, preferably containing 1 or 2 rings. The cyclohydrocarbyl can be of a monocyclic, fused polycyclic, bridged cyclic or spiro cyclic structure. Non-limiting examples of cyclohydrocarbyl groups include, but are not limited to, cyclopropyl, cyclobutyl, cyclopentyl, cyclohexyl, cycloheptyl, bicyclo[2.2.1]heptyl, spiro[3.3]heptyl, and the like.

The term "heterocyclyl" refers to a fully saturated or partially unsaturated (but not fully unsaturated heteroaromatic group) nonaromatic ring which may exist in the form of a monocyclic, bridged cyclic or spiro cyclic structure. Unless otherwise specified, the heterocyclyl is usually a 3-7 membered ring containing 1-3 heteroatoms (preferably 1 or 2 heteroatoms) independently selected from the group consisting of sulfur, oxygen and/or nitrogen. Non-limiting examples of heterocyclyl include, but are not limited to, oxiranyl, tetrahydrofuranyl, dihydrofuranyl, pyrrolidinyl, N-methylpyrrolidinyl, dihydropyrrolyl, piperidinyl, piperazinyl, pyrazolidinyl, 4H-pyranyl, morpholinyl, thiomorpholinyl, tetrahydrothienyl and the like.

The term "heterocycloalkyl" refers to a fully saturated cyclic group that may exist in the form of a monocyclic, bridged cyclic or spiro cyclic structure. Unless otherwise specified, the heterocyclyl is usually a 3-7 membered ring containing 1-3 heteroatoms (preferably 1 or 2 heteroatoms) independently selected from the group consisting of sulfur, oxygen and/or nitrogen. Examples of 3 membered heterocycloalkyl include, but are not limited to, oxiranyl, thiiranyl, and aziranyl; non-limiting examples of 4 membered heterocycloalkyl include, but are not limited to, azetidinyl, oxetanyl, and thietanyl; examples of 5 membered heterocycloalkyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl, and tetrahydropyrazolyl; examples of 6 membered heterocycloalkyl include, but are not limited to, piperidinyl, tetrahydropyranyl, tetrahydrothiopyranyl, morpholinyl, piperazinyl, 1,4-thioxanyl, 1,4-dioxanyl, thiomorpholinyl, 1,3-dithianyl, and 1,4-dithianyl; examples of 7 membered heterocycloalkyl include, but are not limited to, azacycloheptanyl, oxacycloheptanyl and thiocycloheptanyl. Preferably, the heterocycloalkyl is a monocyclic heterocycloalkyl having 5 or 6 ring atoms.

The term "heterocyclohydrocarbyl" refers to a nonaromatic monocyclic, fused polycyclic, bridged cyclic or spiro cyclic group, wherein some ring atoms are heteroatoms selected from the group consisting of N, O, and $S(O)_n$ (n is 0, 1 or 2), while the remaining ring atoms are C. Such a ring can be saturated or unsaturated (for example, with one or more double bonds), but does not have a fully conjugated π-electron system. Examples of 3 membered heterocyclohydrocarbyl include, but are not limited to, oxiranyl, thiiranyl and aziranyl; examples of 4 membered heterocyclohydrocarbyl include, but are not limited to, azetidinyl, oxetanyl and thietanyl; examples of 5 membered heterocyclohydrocarbyl include, but are not limited to, tetrahydrofuranyl, tetrahydrothienyl, pyrrolidinyl, isoxazolidinyl, oxazolidinyl, isothiazolidinyl, 1,1-dioxidoisothiazolidinyl, thiazolidinyl, imidazolidinyl, tetrahydropyrazolyl, pyrrolinyl, dihydrofuranyl and dihydrothienyl; examples of 6 membered heterocyclohydrocarbyl include, but are not limited to, piperidinyl, tetrahydropyranyl, tetrahydrothiapyranyl, morpholinyl, piperazinyl, 1,4-thioxanyl, 1,4-dioxanyl, thiomorpholinyl, 1,2- and 1,4-dithianyl, dihydropyridinyl, tetrahydropyridinyl, dihydropyranyl, tetrahydropyranyl and dihydrothiapyranyl; examples of 7 membered heterocyclohydrocarbyl include, but are not limited to, azacycloheptanyl, oxacycloheptanyl, thiocycloheptanyl, oxaazabicyclo[2.2.1]heptyl, azaspiro[3.3]heptyl and the like.

The term "aryl" refers to an aromatic monocyclic or fused polycyclic group of carbon atoms with the conjugated π-electron system. For example, an aryl may have 6-20 carbon atoms, 6-14 carbon atoms or 6-12 carbon atoms. Non-limiting examples of aryl include, but are not limited to, phenyl, naphthyl, anthryl, 1,2,3,4-tetrahydronaphthalenyl, and the like.

The term "heteroaryl" refers to a monocyclic or fused polycyclic system containing at least one ring atom selected from the group consisting of N, O and S, with the remaining ring atoms being C, and having at least one aromatic ring. Preferably, heteroaryl has a single 5-8 membered ring, or a fused polycyclic system containing 6-14 ring atoms, in particular 6-10 ring atoms. Non-limiting examples of heteroaryl include, but are not limited to, pyrrolyl, furanyl, thienyl, imidazolyl, oxazolyl, pyrazolyl, pyridinyl, pyrimidinyl, pyrazinyl, quinolyl, isoquinolyl, tetrazolyl, triazolyl, triazinyl, benzofuranyl, benzothienyl, indolyl, isoindolyl and the like.

The compound disclosed herein can be asymmetrical, for example, has one or more stereoisomers. Unless otherwise stated, all stereoisomers are included, for example, enantiomers and diastereoisomers. The compound with asymmetric carbon atoms disclosed herein can be separated in an optically pure form or in a racemic form. The optically pure form can be separated from a racemic mixture or can be synthesized using a chiral raw material or a chiral reagent.

The terms "administer", "administration" and "administering" refer to physically introducing the composition comprising a therapeutic agent to an entity using any of various methods and delivery systems known to those skilled in the art.

The term "treating" and "treatment" usually refers to acquiring needed pharmacological effect and/or physiological effect. In terms of partially or fully stabilizing or curing the disease and/or a side effect of the disease, the effect can be therapeutic. As used herein, "treating" and "treatment" encompasses any treatment of a disease in a patient, including (a) inhibiting a symptom of the disease, i.e., blocking the progression of the disease; or (b) alleviating a symptom of the disease, i.e., causing remission of the disease or the symptom.

The term "effective amount" refers to an amount of the compound disclosed herein for (i) treating or preventing a specific disease, condition or disorder; (ii) alleviating, relieving or eliminating one or more symptoms of a specific disease, condition or disorder, or (iii) preventing or delaying onset of one or more symptoms of a specific disease, condition or disorder disclosed herein. The amount of the compound disclosed herein composing the "therapeutically effective amount" varies dependently on the compound, the disease state and its severity, the mode of administration, and the age of the mammal to be treated, but can be determined routinely by those skilled in the art in accordance with their knowledge and the present disclosure.

The term "subject" can be a mammal. In some embodiments, the subject is a mouse. In some embodiments, the subject is a human.

As used herein, the compound of formula I or the pharmaceutically acceptable salt thereof may be administered by any applicable routes and methods, for example, oral administration or parenteral (for example, intravenous) administration. The therapeutically effective amount of the compound of formula I or the pharmaceutically acceptable salt thereof includes, but is not limited to, from about 0.0001 to 20 mg/kg/d, for example, from 0.001 to 10 mg/kg/d. The dosing frequency (e.g., once, twice or more times daily) of the compound of formula I or the pharmaceutically acceptable salt thereof can be determined according to the requirements of the patient individuals, comprising the severity of the disease, the response of the disease, any treatment-related toxicity, and the age and health of the patient. Administration can be intermittent, for example, in a period of several days, the subject receives a daily dosage of the compound of formula I or the pharmaceutically acceptable salt thereof, and in the following period of the several days or more days, the patient does not receive the daily dosage of the compound of formula I or the pharmaceutically acceptable salt thereof.

Entecavir can be administered in various routes including, but not limited to, oral, parenteral, intraperitoneal, intravenous, intra-arterial, transdermal, sublingual, intramuscular, rectal, transbuccal, intranasal, inhalational, vaginal, intraocular, topical, subcutaneous, intralipid, intraarticular, intraperitoneal and intrathecal administrations. In some specific embodiments, the drug is administered orally. The amount of entecavir administered can be determined according to the severity of the disease, the response of the disease, any treatment-related toxicity, and the age and health of a patient. For example, a daily dose for administering entecavir can be 0.005 mg to 10.0 mg. Entecavir can be administered once or more times daily. In some embodiments, entecavir is administered once daily in an oral solid formulation.

The term "about" shall be understood to include within three standard deviations of the mean or within standard ranges of tolerance in the specific art. In some embodiments, the term "about" shall be understood as a variation not exceeding 0.5. The term "about" modifies all listed values thereafter. For example, "about 1, 2 and 3" represents "about 1", "about 2" and "about 3".

The term "pharmaceutical combination" refers to combined use of two or more active ingredients in a simultaneous, concurrent or sequential manner.

The term "fixed combination" refers to the active ingredients (such as TLR7 agonists or entecavir) are administered to a subject simultaneously in a fixed total dose or dose ratio, or in the form of a single entity, pharmaceutical composition or formulation. In some embodiments, for example, the active ingredients are in the same tablet or the same capsule or the same sachet.

The term "non-fixed combination" refers to two or more active ingredients as independent entities (such as pharmaceutical compositions, pharmaceutical preparations) administered to an individual simultaneously, concurrently or sequentially without any specific time limit, wherein the active ingredients administered to the individual reach therapeutically effective amounts. An example, which can be enumerated, of the non-fixed combination is a cocktail therapy, for example, 2, 3 or more active ingredients are administered. In a non-fixed combination, each active ingredient can be packaged, sold or administered as a fully independent pharmaceutical composition. The "non-fixed combination" further includes combined use of "fixed combinations" the "fixed combination" with any one or more independent entities of active ingredients.

The term "pharmaceutical composition" refers to a mixture comprised of one or more of the compounds or the pharmaceutically acceptable salts thereof, or the pharmaceutical combinations thereof disclosed herein and a pharmaceutically acceptable excipient. The pharmaceutical composition is intended to facilitate the administration of the compound or the pharmaceutical combination thereof disclosed herein to a subject.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to salts of the compounds disclosed herein that are within the definition of "pharmaceutically acceptable".

Unless otherwise specified, terms in the singular shall be deemed to include the plural and vice versa. Unless otherwise specified, the word "a" or "an" refers to "at least one". Unless otherwise stated, use of or means "and/or".

As used herein, the terms "comprise", "comprises" and "comprising" or equivalents thereof are open-ended statements and mean that elements, components and steps that are not specified may be included in addition to those listed, unless otherwise stated.

All patents, patent applications and other identified publications are expressly incorporated herein by reference for the purpose of description and disclosure. These publications are provided solely because they were disclosed prior to the filing date of the present application. All statements as to the dates of these documents or description as to the contents of these documents are based on the information available to the applicant and do not constitute any admission as to the correctness of the dates or the content of these documents. Moreover, in any country or region, any reference to these publications herein is not to be construed as an admission that the publications form part of the commonly recognized knowledge in the art.

Administration

The content below is not intended to limit the administration of the pharmaceutical combination disclosed herein. The active ingredients in the pharmaceutical combination disclosed herein can be formulated separately, or some or all of the active ingredients are co-formulated. In one embodiment, the pharmaceutical combination disclosed herein can be formulated into a pharmaceutical composition which is suitable for a single dose or multiple doses.

The active ingredients in the pharmaceutical combination disclosed herein can be administered separately, or some or all of the active ingredients are co-administered. The ingredients of the pharmaceutical combination disclosed herein can be administered in a substantially asynchronous manner, or some or all of the ingredients are administered in a substantially synchronous manner.

The active ingredients in the pharmaceutical combination disclosed herein can be administered independently, or some or all of the active ingredients are co-administered in various proper routes, including, but not limited to, oral administration or parenteral administration (intravenous, intramuscular, local or subcutaneous routes). In some embodiments, the active ingredients in the pharmaceutical combination disclosed herein can be administered independently, or some or all of the active ingredients are co-administered by means of oral administration or injection, for example, intravenous injection or intraperitoneal injection.

The active ingredients in the pharmaceutical combination disclosed herein can be in independent suitable dosage forms, or some or all of the active ingredients are co-formulated in a suitable dosage form, including, but not limited to, tablet, lozenge, pill, capsule (for example, hard capsule, soft capsule, enteric capsule and microcapsule), elixir, granule, syrup, injection (intramuscular, intravenous and intraperitoneal), powder, emulsion, suspension, solution, dispersion and dosage forms of sustained-release preparations for oral or non-oral administration.

The active ingredients in the pharmaceutical combination disclosed herein can be each independently formulated with a pharmaceutically acceptable carrier and/or excipient, or some or all of the active ingredients are co-formulated with a pharmaceutically acceptable carrier and/or excipient.

The pharmaceutical combination disclosed herein may further comprise an additional therapeutic agent. In one embodiment, the additional therapeutic agent can be a therapeutic agent known in the art for treating hepatitis B virus infection.

In some embodiments, the effective amounts of the compound of formula I or the pharmaceutically acceptable salt thereof and entecavir or the pharmaceutically acceptable salt or solvate thereof disclosed herein can be administered to a subject in need thereof simultaneously, sequentially or at intervals.

In some embodiments, the effective amounts of the compound of formula I or the pharmaceutically acceptable salt thereof and entecavir or the pharmaceutically acceptable salt or solvate thereof can be administered to a subject in need thereof in the same regimen or in different regimens.

In some embodiments, the compound of formula I or the pharmaceutically acceptable salt thereof is administered thrice every day, twice every day, once every day, once every two days, once every three days, once every four days, once every five days, once every six days, once every week, once every two weeks or once every three weeks.

In some embodiments, the compound of formula I or the pharmaceutically acceptable salt thereof is administered at a dose of 0.1 to 10.0 mg each time, preferably a dose of 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, 10.0 mg, or a range formed by any of the values.

In some embodiments, the compound of formula I or the pharmaceutically acceptable salt thereof is administered at a dose of 0.2 to 5.0 mg, 0.4 to 4.0 mg, 0.5 to 3.0 mg, 0.6 to 2.6 mg, 0.8 to 2.2 mg, 0.8 to 1.8 mg, 1.0 to 2.0 mg, 1.0 to 1.8 mg or 1.0 to 1.6 mg each time.

In some embodiments, the compound of formula I or the pharmaceutically acceptable salt thereof is administered once every week at a dose of 0.2 to 5.0 mg, 0.4 to 4.0 mg, 0.5 to 3.0 mg, 0.6 to 2.6 mg, 0.8 to 2.2 mg, 0.8 to 1.8 mg, 1.0 to 2.0 mg, 1.0 to 1.8 mg or 1.0 to 1.6 mg each time. In some embodiments, the compound of formula I or the pharmaceutically acceptable salt thereof is administered once every week at a dose of 1.0 to 1.8 mg each time.

In some embodiments, entecavir or the pharmaceutically acceptable salt or solvate thereof is administered thrice every day, twice every day, once every day, once every two days, once every three days, once every four days, once every five days, once every six days, once every week, once every two weeks or once every three weeks.

In some embodiments, entecavir or the pharmaceutically acceptable salt or solvate thereof is administered at a dose of 0.005 mg to 5.0 mg each time, preferably a dose of 0.01 mg, 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, or a range formed by any of the values. In some embodiments, entecavir or the pharmaceutically acceptable salt or solvate thereof is administered at a dose of 0.05 mg to 5.0 mg, 0.10 mg to 2.0 mg, 0.25 mg to 2.0 mg or 0.5 mg to 1.0 mg each time.

In some embodiments, entecavir or the pharmaceutically acceptable salt or solvate thereof is administered once daily at a dose of 0.10 mg to 2.0 mg each time. In some embodiments, entecavir or the pharmaceutically acceptable salt or solvate thereof can be administered once daily at a dose of 0.5 mg each time.

In some embodiments, the TLR7 agonist (i.e., the compound of formula I) is administered once every week at a dose of 1.0 to 1.8 mg each time; entecavir is administered once every day at a dose of 0.5 mg each time.

Technical Effects

The pharmaceutical composition can significantly reduce the HBV DNA level or relieve other HBV markers. In addition, the pharmaceutical combination disclosed herein demonstrates a significant enhancement compared to monotherapies. These indicate that the pharmaceutical combination disclosed herein has good pharmaceutical value.

DRAWING OF THE SPECIFICATION

FIG. 1 illustrates effect of a TLR7 agonist on serum HBV DNA replication levels in AAV mice.

DETAILED DESCRIPTION

For the sake of clarity, the present application is further illustrated by examples, which are, however, not intended to limit the scope of the present application. All reagents are commercially available and can be used without further purification.

Example 1. AAV Mice Study

1.1. Test Compounds

In this example, the TLR7 agonist was

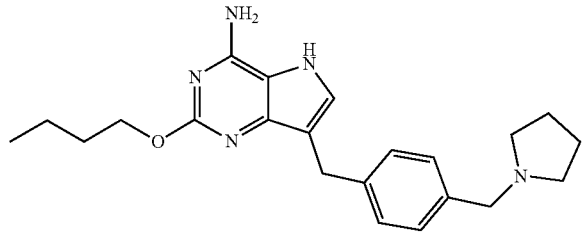 [SMILES: CCCCOc1nc(N)c2[nH]cc(Cc3ccc(CN4CCCC4)cc3)c2n1]

(2-butoxy-7-(4-(pyrrolidin-1-ylmethyl) benzyl)-5H-pyrrolo[3,2-d]pyrimidin-4-amine); see WO2016023511 for the preparation method.

In this example, the entecavir used is a monohydrate thereof.

1.2. Method and Grouping

Male C57BL/6 mice (Shanghai Slac Laboratory Animal Co., Ltd.) aged 6-8 weeks were taken, and rAAV8-1.3HBV virus (FivePlus Institute of Molecular Medicine, Beijing) was injected into the C57BL/6 mice via tail veins at a dose of $1\times10^{11}$ vg. Blood was collected from the orbit at week 2 and week 4 after the virus was injected. Serum was separated, and HBV DNA copy number in serum were measured to determine whether the model was successfully constructed or not. Mice were randomized according to the HBV DNA copy number into vehicle control group, TLR7 agonist group (20 mg/kg, tiw), entecavir (ETV) group (0.0032 (week 1, 1 W) & 0.001 (week 2-6, 2-6 W) mg/kg, qd), and TLR7 agonist and ETV combination group, each group containing 6 mice. The mice in each group were administered intragastrically for 6 weeks, and the administration was stopped for 3 week. Blood was collected from the orbit at weeks 1, 2, 3, 4, 5 and 6 during the administration period and weeks 1, 2 and 3 during the withdrawal period, and serum was separated. The HBV DNA copy number was determined by fluorescence quantitative PCR.

Groups:
i. Vehicle control group;
ii. Monotherapy group: entecavir;
iii. Monotherapy group: TLR7 agonist;
iv. Combination group (combo): TLR7 agonist and entecavir;

TABLE 1-1

Dosing regimen

| Group | Dosage (mg/kg) | Administration Route | Administration interval | Administration cycle |
|---|---|---|---|---|
| i. | — | i.g. | qd | 6 w |
| ii. | 0.0032 (1 W) & 0.001 (2-6 W) | i.g. | qd | 6 w |
| iii. | 20 (TLR7 agonist) | i.g. | tiw | 6 w |
| iv. | 20 (TLR7 agonist) | i.g. | tiw | 6 w |
|  | 0.0032 (1 W) & 0.001 (2-6 W) (entecavir) | i.g. | qd | 6 w |

Note:
i.g.: intragastric;
qd: once daily;
tiw: once every three days;
6 w: six weeks.
The administration of the combination group was consistent with that of the monotherapy groups.

1.3. Method for Evaluating Pharmaceutical Combination

The test results were evaluated by Jin equation. The Jin equation is a modified method based on the Burgi method, and is also referred to the probability addition method:

The combination efficacy is calculated according to the following equation: $q=E_{A+B}/(E_A+E_B-E_A\times E_B)$ wherein $E_A$ denotes the efficacy of drug A monotherapy; $E_B$ denotes the efficacy of drug B monotherapy; $E_{A+B}$ denotes the efficacy of the combination of drugs A and B.

The significance of q: 0.85 to 1.15 indicates simple addition; 1.15 to 20 indicates enhancement; greater than 20 indicates significant enhancement; 0.85 to 0.55 indicates antagonism; less than 0.55 indicates significant antagonism. The q value takes the absolute value.

1.4. Results

The results are shown in Table 1-2, Table 1-3, Table 1-4 and FIG. 1.

TABLE 1-2

Efficacy of different therapies on HBV DNA replication level (logic IU/mL) in mouse serum (treatment period)

| Group | Treatment period (d) | | | | | | |
|---|---|---|---|---|---|---|---|
| | 0 | 7 | 14 | 21 | 28 | 35 | 42 |
| i. | 7.57 ± 0.17 | 7.31 ± 0.23 | 7.31 ± 0.31 | 6.79 ± 0.47 | 6.72 ± 0.53 | 6.95 ± 0.58 | 7.23 ± 0.67 |
| ii. | 7.53 ± 0.15 | 5.27 ± 0.18*** | 5.66 ± 0.14*** | 5.96 ± 0.28*** | 5.34 ± 0.43*** | 5.62 ± 0.36*** | 6.44 ± 0.46* |
| iii. | 7.53 ± 0.15 | 6.64 ± 1.33*** | 4.55 ± 1.41*** | 4.13 ± 0.67*** | 3.64 ± 0.21*** | 3.61 ± 0.24*** | 3.41 ± 0.33*** |
| iv. | 7.50 ± 0.13 | 4.15 ± 0.76*** | 2.48 ± 0.81*** | 2.62 ± 0.74*** | 1.82 ± 0.54*** | 2.32 ± 0.16*** | 2.42 ± 0.31*** |

Note:
comparison with the vehicle control group, where * P < 0.05, P < 0.01, * P < 0.001.

TABLE 1-3

Efficacy of different therapies on HBV DNA replication level ($\log_{10}$ IU/mL) in mouse serum (withdrawal period)

| Group | Withdrawal period (d) | | |
|---|---|---|---|
| | 49 | 56 | 63 |
| i. | 7.40 ± 0.49 | 7.51 ± 0.48 | 7.54 ± 0.34 |
| ii. | 6.97 ± 0.72 | 7.32 ± 0.73 | 7.33 ± 0.80 |
| iii. | 4.37 ± 0.48*** | 4.86 ± 0.41*** | 5.26 ± 0.39*** |
| iv. | 3.60 ± 0.32*** | 3.96 ± 0.55*** | 5.71 ± 0.68*** |

Note:
comparison with the vehicle control group, where *P < 0.05, P < 0.01, *P < 0.001

TABLE 1-4

Evaluation of combination therapy by Jin equation

| | Treatment period (d) | | | | | |
|---|---|---|---|---|---|---|
| | 7 | 14 | 21 | 28 | 35 | 42 |
| q value | 2.35 | 33.54 | 3.25 | 23.38 | 20.32 | 3.02 |

Over a 42-day treatment period, HBV DNA was significantly reduced in the monotherapy groups of entecavir and TLR7 agonist (groups ii and iii); the combination group (group iv) also demonstrated significantly reduced HBV DNA, and q-value results indicated that the combination therapy exhibited superior synergic effect.

Example 2

1. Test Compounds
In this example, the TLR7 agonist was

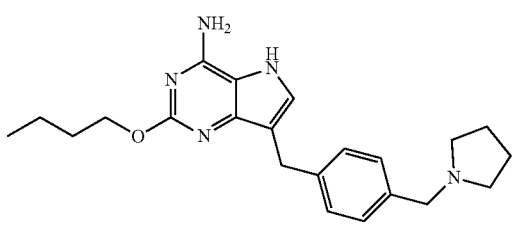 [SMILES: CCCCOc1nc(N)c2[nH]cc(Cc3ccc(CN4CCCC4)cc3)c2n1]

(2-butoxy-7-(4-(pyrrolidin-1-ylmethyl) benzyl)-5H-pyrrolo[3,2-d]pyrimidin-4-amine); see WO2016023511 for the preparation method. The compound was prepared into tablets with strength of 0.2 mg or 0.5 mg.

Entecavir: commercially available entecavir tablets with strength of 0.5 mg. Commercially available entecavir tablets include, but are not limited to, entecavir dispersible tablets (Runzhong).

Placebo: a placebo for TLR7 agonist.

2. Enrolled Subjects
The subject should meet all of the following criteria:
1) Male patients or non-pregnant, non-lactating female patients aged 18-65 years (inclusive);
2) Serum virology: persistent positive serum HBsAg for 6 months or more, or with evidence of chronic hepatitis B for 6 months;
3) Previously treated patients: historical HBV DNA inhibition less than the lower limit of normal 24 weeks before enrollment, and HBV DNA inhibition defined as <69 IU/mL determined by a Roche reagent during screening; Fibroscan ≤9.0 Kpa (fasting), and ALT≤5× ULN;
4) Previously untreated patients: HBV DNA >$10^5$ copies/mL (or >20000 IU/mL) for HBeAg-positive chronic hepatitis B patients or HBV DNA >$10^4$ copies/mL (or >2000 IU/mL) for HBeAg-negative patients as determined by Roche's Cobas Taqman real-time quantitative PCR test v2.0, with the lower limit of detection being 20 IU/mL; Fibroscan ≤12.4 Kpa (fasting), and 1×ULN-≤ALT≤5×ULN. The previously untreated patients mean that the patients did not receive antiviral therapies against HBV or participate in related clinical trials.

3. Dosage and Administration
TLR7 agonist: once weekly.
Entecavir: 0.5 mg/day, once daily.
The first group included 12 subjects, of which 8 received 1.2 mg of the TLR7 agonist in combination with entecavir and 4 received placebo in combination with entecavir for 24 weeks.

The second, third and fourth groups each included 36 subjects randomly subgrouped in a ratio of TLR7 agonist:placebo=5:1. The three groups respectively received 1.0 mg of TLR7 agonist combined with entecavir or placebo combined with entecavir (the second group), 1.5 mg of TLR7 agonist combined with entecavir or placebo combined with entecavir (the third group), and 1.8 mg of TLR7 agonist combined with entecavir or placebo combined with entecavir (the fourth group). The groups were treated for 24 weeks.

4. Efficacy Endpoints
Efficacy endpoints: serum HBsAg, HBeAg, or HBV DNA, etc.
Exploratory endpoints: HBV RNA and HBcrAg, etc.

The mean, standard deviation, median, quartile, minimum and maximum values were used to describe the average content of the index parameters at each detection time point in each group and the change from baseline; the mixed-effects model for repeated measures (MMRM) was used, with group, baseline, detection time point, and the interaction term of group and detection time point as fixed effects and the subject and the intercept term as random effects, the changes from baseline of the index parameters at each detection time point in treatment group were compared with those of the placebo groups, respectively, and corrected by the Dunnett's test.

5. Results

All of the TLR7 agonist and entecavir combination groups showed significantly inhibition on HBV DNA replication. All of the TLR7 agonist and placebo combinations achieved inhibition of HBV DNA replication. The entecavir and placebo combinations also had inhibitory effects on HBV DNA replication.

The invention claimed is:

1. A pharmaceutical combination, comprising a compound of formula I or a pharmaceutically acceptable salt thereof and entecavir or a pharmaceutically acceptable salt or solvate thereof, wherein the compound of formula I is shown as follows:

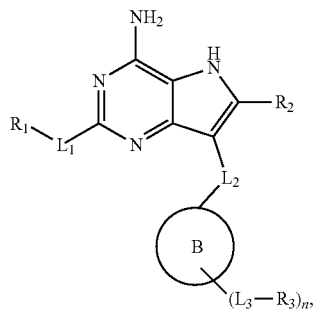

I wherein,
$L_1$ is selected from —O—;
$L_2$ is selected from —$CH_2$—, wherein the —$CH_2$— is optionally substituted with $R_4$;
$R_1$ is selected from the group consisting of hydrogen and $C_{1-10}$ alkyl, wherein the $C_{1-10}$ alkyl is optionally substituted with $R_5$;
$R_2$ is selected from the group consisting of hydrogen, cyano, —COOH and —$CONH_2$, wherein the —COOH and —$CONH_2$ are optionally substituted with $R_6$;
B is selected from the group consisting of 6-10 membered aryl and 5-10 membered heteroaryl;
$L_3$ is selected from the group consisting of $C_{0-6}$ alkylene and imino, wherein the $C_{0-6}$ alkylene and imino are optionally substituted with $R_7$;
$R_3$ is selected from the group consisting of hydrogen, amino, $C_{1-10}$ alkyl, $C_{3-10}$ cyclohydrocarbyl, 3-10 membered heterocyclohydrocarbyl, 6-10 membered aryl and 5-10 membered heteroaryl, wherein the amino, $C_{1-10}$ alkyl, $C_{3-10}$ cyclohydrocarbyl, 3-10 membered heterocyclohydrocarbyl, 6-10 membered aryl and 5-10 membered heteroaryl are optionally substituted with $R_8$, or $R_3$ and $L_3$, together with an ortho atom on ring B, form a saturated or unsaturated 5-8 membered ring, wherein the 5-8 membered ring is optionally substituted with $R_9$;
n is 0, 1, 2, 3, 4 or 5;
$R_4$, $R_5$, $R_6$, $R_7$, $R_8$ and $R_9$ are each independently selected from halogen, cyano, hydroxy, sulfydryl, amino, —R, —OR, —O, —SR, —NHR and —$NR_2$; R is independently selected from the group consisting of $C_{1-8}$ alkyl, $C_{3-8}$ cyclohydrocarbyl, 3-8 membered heterocyclohydrocarbyl, 6-8 membered aryl and 5-8 membered heteroaryl.

2. The pharmaceutical combination according to claim 1, wherein the compound of formula I or the pharmaceutically acceptable salt thereof is selected from the group consisting of:

2-butoxy-7-(3-((4-methylpiperazin-1-yl)methyl)benzyl)-5H-pyrrolo[3,2-d]pyrimidin-4-amine;
2-butoxy-7-(3-(morpholinomethyl)benzyl)-5H-pyrrolo[3,2-d]pyrimidin-4-amine;
7-(3-(aminomethyl)benzyl)-2-butoxy-5H-pyrrolo[3,2-d]pyrimidin-4-amine;
2-butoxy-7-(3-(pyrrolidin-1-ylmethyl)benzyl)-5H-pyrrolo[3,2-d]pyrimidin-4-amine;
2-butoxy-7-(4-((3,3-difluoropyrrolidin-1-yl)methyl)benzyl)-5H-pyrrolo[3,2-d]pyrimidin-4-amine;
2-butoxy-7-(4-((3-fluoropyrrolidin-1-yl)methyl)benzyl)-5H-pyrrolo[3,2-d]pyrimidin-4-amine;
1-(4-((4-amino-2-butoxy-5H-pyrrolo[3,2-d]pyrimidin-7-yl)methyl)benzyl) pyrrolidin-3-ol;
2-butoxy-7-(4-(piperidin-1-ylmethyl)benzyl)-5H-pyrrolo[3,2-d]pyrimidin-4-amine;
2-butoxy-7-(4-(morpholinomethyl)benzyl)-5H-pyrrolo[3,2-d]pyrimidin-4-amine;
2-butoxy-7-(4-((4-methylpiperazin-1-yl)methyl)benzyl)-5H-pyrrolo[3,2-d]pyrimidin-4-amine;
2-butoxy-7-(4-((dimethylamino)methyl)benzyl)-5H-pyrrolo[3,2-d]pyrimidin-4-amine;
2-butoxy-7-(4-((diethylamino)methyl)benzyl)-5H-pyrrolo[3,2-d]pyrimidin-4-amine;
2-butoxy-7-(4-((dipropylamino)methyl)benzyl)-5H-pyrrolo[3,2-d]pyrimidin-4-amine;
7-(4-(azetidin-1-ylmethyl)benzyl)-2-butoxy-5H-pyrrolo[3,2-d]pyrimidin-4-amine;
2-butoxy-7-(4-((3-methoxyazetidin-1-yl)methyl)benzyl)-5H-pyrrolo[3,2-d]pyrimidin-4-amine;
2-butoxy-7-(4-(4-methyl-1,4-diazepan-1-ylmethyl)benzyl)-5H-pyrrolo[3,2-d]pyrimidin-4-amine;
2-butoxy-7-(4-((2,6-dimethylmorpholino)methyl)benzyl)-5H-pyrrolo[3,2-d]pyrimidin-4-amine;
7-(4-((1S,4S)-2-oxa-5-azabicyclo[2.2.1]heptan-5-ylmethyl)benzyl)-2-butoxy-5H-pyrrolo[3,2-d]pyrimidin-4-amine;
2-butoxy-7-(4-((4-methoxypiperidin-1-yl)methyl)benzyl)-5H-pyrrolo[3,2-d]pyrimidin-4-amine;
2-butoxy-7-(4-((4-isopropylpiperazin-1-yl)methyl)benzyl)-5H-pyrrolo[3,2-d]pyrimidin-4-amine;
2-butoxy-7-(4-(pyrrolidin-1-ylmethyl)benzyl)-5H-pyrrolo[3,2-d]pyrimidin-4-amine;
2-butoxy-7-((6-(pyrrolidin-1-ylmethyl) pyridin-3-yl)methyl)-5H-pyrrolo[3,2-d]pyrimidin-4-amine;
2-butoxy-7-(3-(2-(pyrrolidin-1-yl)ethyl)benzyl)-5H-pyrrolo[3,2-d]pyrimidin-4-amine;
2-butoxy-7-(4-(1-(pyrrolidin-1-yl)ethyl)benzyl)-5H-pyrrolo[3,2-d]pyrimidin-4-amine;
2-butoxy-7-(4-(1-methylpiperidin-4-yl)benzyl)-5H-pyrrolo[3,2-d]pyrimidin-4-amine;

2-butoxy-7-(4-(1-methylpyrrolidin-2-yl)benzyl)-5H-pyr-rolo[3,2-d]pyrimidin-4-amine;
1-(4-((4-amino-2-butoxy-5H-pyrrolo[3,2-d]pyrimidin-7-yl)methyl)phenyl)-4-methylpiperazin-2-one;
7-benzyl-2-(2-methoxyethoxy)-5H-pyrrolo[3,2-d]pyrimidin-4-amine;
2-(2-methoxyethoxy)-7-((6-methylpyridin-3-yl)methyl)-5H-pyrrolo[3,2-d]pyrimidin-4-amine;
7-((5-chloropyridin-2-yl)methyl)-2-(2-methoxyethoxy)-5H-pyrrolo[3,2-d]pyrimidin-4-amine;
2-(2-methoxyethoxy)-7-((6-(pyrrolidin-1-ylmethyl) pyridin-3-yl)methyl)-5H-pyrrolo[3,2-d]pyrimidin-4-amine;
1-(4-((4-amino-2-(2-methoxyethoxy)-5H-pyrrolo[3,2-d]pyrimidin-7-yl)methyl)phenyl)-4-methylpiperazin-2-one;
2-butoxy-7-((5-(pyrrolidin-1-ylmethyl) pyridin-2-yl)methyl)-5H-pyrrolo[3,2-d]pyrimidin-4-amine;
4-amino-2-butoxy-7-((6-(pyrrolidin-1-ylmethyl) pyridin-3-yl)methyl)-5H-pyrrolo[3,2-d]pyrimidin-6-carbonitrile;
4-amino-2-butoxy-7-(4-(pyrrolidin-1-ylmethyl)benzyl)-5H-pyrrolo[3,2-d]pyrimidin-6-carbonitrile;
4-amino-2-butoxy-7-(4-(morpholinomethyl)benzyl)-5H-pyrrolo[3,2-d]pyrimidin-6-carbonitrile;
4-amino-2-butoxy-7-(4-((4-methylpiperazin-1-yl)methyl)benzyl)-5H-pyrrolo[3,2-d]pyrimidin-6-carbonitrile;
4-amino-2-butoxy-7-(4-(pyrrolidin-1-ylmethyl)benzyl)-5H-pyrrolo[3,2-d]pyrimidin-6-carboxamide;
2-butoxy-7-((1,2,3,4-tetrahydroisoquinolin-7-yl)methyl)-5H-pyrrolo[3,2-d]pyrimidin-4-amine;
2-butoxy-7-((2-methyl-1,2,3,4-tetrahydroisoquinolin-7-yl)methyl)-5H-pyrrolo[3,2-d]pyrimidin-4-amine;
2-butoxy-7-((2-ethyl-1,2,3,4-tetrahydroisoquinolin-7-yl)methyl)-5H-pyrrolo[3,2-d]pyrimidin-4-amine;
2-butoxy-7-((2-isopropyl-1,2,3,4-tetrahydroisoquinolin-7-yl)methyl)-5H-pyrrolo[3,2-d]pyrimidin-4-amine;
2-butoxy-7-((1,2,3,4-tetrahydroisoquinolin-6-yl)methyl)-5H-pyrrolo[3,2-d]pyrimidin-4-amine;
2-butoxy-7-((2-methyl-1,2,3,4-tetrahydroisoquinolin-6-yl)methyl)-5H-pyrrolo[3,2-d]pyrimidin-4-amine;
2-butoxy-7-((2-ethyl-1,2,3,4-tetrahydroisoquinolin-6-yl)methyl)-5H-pyrrolo[3,2-d]pyrimidin-4-amine; and
2-butoxy-7-((2-(pyrrolidin-1-ylmethyl) thiazol-5-yl)methyl)-5H-pyrrolo[3,2-d]pyrimidin-4-amine, or a pharmaceutically acceptable salt thereof.

3. The pharmaceutical combination according to claim 1, wherein the compound of formula I in the pharmaceutical combination is selected from a compound of formula A:

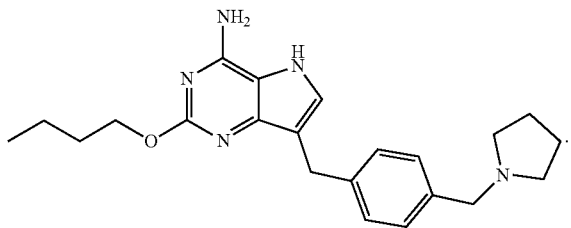 [SMILES: CCCCOc1nc(N)c2[nH]cc(Cc3ccc(CN4CCCC4)cc3)c2n1]

4. The pharmaceutical combination according to claim 1, wherein entecavir or the pharmaceutically acceptable salt or solvate thereof is selected from the group consisting of entecavir maleate, entecavir monomaleate, entecavir hydrate, entecavir 0.5-2 hydrate, and entecavir monohydrate.

5. The pharmaceutical combination according to claim 4, wherein entecavir or the pharmaceutically acceptable salt or solvate thereof is selected from entecavir monomaleate monohydrate.

6. The pharmaceutical combination according to claim 1, wherein an average daily dose ratio of the compound of formula I or the pharmaceutically acceptable salt thereof to entecavir or the pharmaceutically acceptable salt or solvate thereof in the pharmaceutical combination is selected from 10:1 to 1:10.

7. The pharmaceutical combination according to claim 6, wherein the average daily dose ratio is selected from the group consisting of 1:1.5 to 1:4, 1:1.6 to 1:3.8, 1:1.8 to 1:3.8, 1:1.8 to 1:3.6 and 1:2 to 1:3.5.

8. The pharmaceutical combination according to claim 1, wherein the compound of formula I or the pharmaceutically acceptable salt thereof in the pharmaceutical combination is administered thrice every day, twice every day, once every day, once every two days, once every three days, once every four days, once every five days, once every six days, once every week, once every two weeks or once every three weeks.

9. The pharmaceutical combination according to claim 1, wherein the compound of formula I or the pharmaceutically acceptable salt thereof in the pharmaceutical combination is administered at a dose of 0.1 to 10.0 mg each time.

10. The pharmaceutical combination according to claim 9, wherein the compound of formula I or the pharmaceutically acceptable salt thereof is administered at a dose of 0.2 to 5.0 mg, 0.4 to 4.0 mg, 0.5 to 3.0 mg, 0.6 to 2.6 mg, 0.8 to 2.2 mg, 0.8 to 1.8 mg, 1.0 to 2.0 mg, 1.0 to 1.8 mg, or 1.0 to 1.6 mg each time.

11. The pharmaceutical combination according to claim 1, wherein entecavir or the pharmaceutically acceptable salt or solvate thereof in the pharmaceutical combination is administered thrice every day, twice every day, once every day, once every two days, once every three days, once every four days, once every five days, once every six days, once every week, once every two weeks or once every three weeks.

12. The pharmaceutical combination according to claim 1, wherein entecavir or the pharmaceutically acceptable salt or solvate thereof in the pharmaceutical combination is administered at a dose of 0.005 mg to 5.0 mg each time.

13. The pharmaceutical combination according to claim 12, wherein entecavir or the pharmaceutically acceptable salt or solvate thereof is administered at a dose of 0.05 mg to 5.0 mg, 0.10 mg to 2.0 mg, 0.25 mg to 2.0 mg, or 0.5 mg to 1.0 mg each time.

14. The pharmaceutical combination according to claim 1, wherein the pharmaceutical combination is a fixed combination; or, the fixed combination is in the form of a solid pharmaceutical composition; or, the compound of formula I or the pharmaceutically acceptable salt thereof and entecavir or the pharmaceutically acceptable salt or solvate thereof in the fixed combination are present in the same solid pharmaceutical composition.

15. The pharmaceutical combination according to claim 14, wherein the solid pharmaceutical composition is selected from the group consisting of a tablet and a capsule.

16. The pharmaceutical combination according to claim 1, wherein the pharmaceutical combination is a non-fixed combination; or, the compound of formula I or the pharmaceutically acceptable salt thereof and entecavir or the pharmaceutically acceptable salt or solvate thereof in the non-fixed combination are each in the form of a solid pharmaceutical composition; or, the compound of formula I or the pharmaceutically acceptable salt thereof and entecavir or the pharmaceutically acceptable salt or solvate thereof in the non-fixed combination are each in the form of a solid pharmaceutical composition, and the solid pharmaceutical composition of the compound of formula I or the pharmaceutically acceptable salt thereof and the solid pharmaceutical composition of entecavir or the pharmaceutically acceptable salt or solvate thereof are present in the same sachet; or, the compound of formula I or the pharmaceutically acceptable salt thereof and entecavir or the pharmaceutically acceptable salt or solvate thereof in the non-fixed combination are each in the form of a solid pharmaceutical composition, and the solid pharmaceutical composition of the compound of formula I or the pharmaceutically acceptable salt thereof and the solid pharmaceutical composition of entecavir or the pharmaceutically acceptable salt or solvate thereof are not present in the same sachet.

17. The pharmaceutical combination according to claim 16, wherein the solid pharmaceutical composition is selected from the group consisting of a tablet and a capsule.

18. A method of treating hepatitis B virus infection, comprising administering to a subject in need thereof an effective amount of the pharmaceutical combination according to claim 1.

19. A kit for treating hepatitis B virus infection, comprising: (a) a first pharmaceutical composition comprising a compound of formula I or the pharmaceutically acceptable salt thereof as active ingredient; (b) a second pharmaceutical composition comprising entecavir or the solvate thereof as active ingredient; and optionally, (c) a package insert for combined use of the compound of formula I or the pharmaceutically acceptable salt thereof and entecavir or the pharmaceutically acceptable salt or solvate thereof,

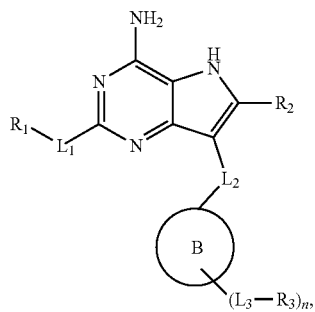

I wherein, $L_1$ is selected from —O—;

$L_2$ is selected from —$CH_2$—, wherein the —$CH_2$— is optionally substituted with $R_4$;

$R_1$ is selected from the group consisting of hydrogen and $C_{1-10}$ alkyl, wherein the $C_{1-10}$ alkyl is optionally substituted with $R_5$;

$R_2$ is selected from the group consisting of hydrogen, cyano, —COOH and —$CONH_2$, wherein the —COOH and —$CONH_2$ are optionally substituted with $R_6$;

B is selected from the group consisting of 6-10 membered aryl and 5-10 membered heteroaryl;

$L_3$ is selected from the group consisting of $C_{0-6}$ alkylene and imino, wherein the $C_{0-6}$ alkylene and imino are optionally substituted with $R_7$;

$R_3$ is selected from the group consisting of hydrogen, amino, $C_{1-10}$ alkyl, $C_{3-10}$ cyclohydrocarbyl, 3-10 membered heterocyclohydrocarbyl, 6-10 membered aryl and 5-10 membered heteroaryl, wherein the amino, $C_{1-10}$ alkyl, $C_{3-10}$ cyclohydrocarbyl, 3-10 membered heterocyclohydrocarbyl, 6-10 membered aryl and 5-10 membered heteroaryl are optionally substituted with $R_8$, or $R_3$ and $L_3$, together with an ortho atom on ring B, form a saturated or unsaturated 5-8 membered ring, wherein the 5-8 membered ring is optionally substituted with $R_9$;

n is 0, 1, 2, 3, 4 or 5;

$R_4$, $R_5$, $R_6$, $R_7$, $R_8$ and $R_9$ are each independently selected from halogen, cyano, hydroxy, sulfydryl, amino, —R, —OR, —O, —SR, —NHR and —$NR_2$; R is independently selected from the group consisting of $C_{1-8}$ alkyl, $C_{3-8}$ cyclohydrocarbyl, 3-8 membered heterocyclohydrocarbyl, 6-8 membered aryl and 5-8 membered heteroaryl.

* * * * *

UNITED STATES PATENT AND TRADEMARK OFFICE
CERTIFICATE OF CORRECTION

| | | |
|---|---|---|
| PATENT NO. | : 12,336,996 B2 | Page 1 of 1 |
| APPLICATION NO. | : 17/754099 | |
| DATED | : June 24, 2025 | |
| INVENTOR(S) | : Hongjiang Xu | |

It is certified that error appears in the above-identified patent and that said Letters Patent is hereby corrected as shown below:

In the Specification

In Columns 35-36, Line 2, (Table 1-2), delete "(logic IU/mL)" and insert -- ($\log_{10}$ IU/mL) --.

In the Claims

In Column 38, Claim 1, Line 8, delete "-O" and insert -- =O --.

In Column 42, Claim 19, Line 33, delete "-O" and insert -- =O --.

Signed and Sealed this
Tenth Day of February, 2026

John A. Squires
*Director of the United States Patent and Trademark Office*